United States Patent [19]

Kast et al.

[11] Patent Number: 5,364,833
[45] Date of Patent: Nov. 15, 1994

[54] CYCLOHEXENONE OXIME ETHERS, THEIR PREPARATION AND THEIR USE AS HERBICIDES

[75] Inventors: Juergen Kast, Boehl-Iggelheim; Norbert Meyer, Ladenburg; Ulf Misslitz, Neustadt; Albrecht Harreus, Ludwigshafen; Helmut Walter, Obrigheim; Matthias Gerber, Mutterstadt; Karl-Otto Westphalen, Speyer, all of Germany

[73] Assignee: BASF Aktiengesellschaft, Ludwigshafen, Germany

[21] Appl. No.: 193,885

[22] Filed: Feb. 5, 1994

Related U.S. Application Data

[63] Continuation of Ser. No. 935,359, Aug. 27, 1992, abandoned, which is a continuation of Ser. No. 697,057, May 8, 1991, abandoned.

[30] Foreign Application Priority Data

May 9, 1990 [DE] Germany .................. 4014988

[51] Int. Cl.$^5$ ............................................ A01N 43/16
[52] U.S. Cl. ........................ 504/289; 504/294; 504/318; 504/326; 504/244
[58] Field of Search ............. 504/289, 294, 244, 318, 504/326

[56] References Cited

U.S. PATENT DOCUMENTS 4,880,456 11/1989 Kolassa et al. ................... 71/88
5,022,914 6/1991 Kast et al. ....................... 71/88

FOREIGN PATENT DOCUMENTS 2001842 10/1989 Canada .
0080301 6/1983 European Pat. Off. .
0125094 11/1984 European Pat. Off. .
0131875 1/1985 European Pat. Off. .
0133349 2/1985 European Pat. Off. .
0218233 4/1987 European Pat. Off. .
0243313 4/1987 European Pat. Off. .

Primary Examiner—Gary E. Hollinden
Assistant Examiner—Brian M. Burn
Attorney, Agent, or Firm—Keil & Weinkauf

[57] ABSTRACT

Cyclohexenone oxime ethers of the formula I

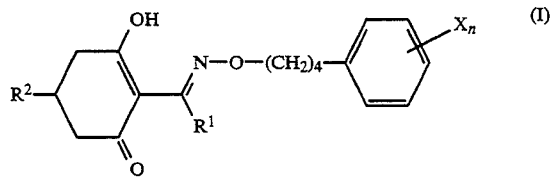

where
R$^1$ is alkyl,
X is halogen,
n is from 1 to 5,
R$^2$ is alkoxyalkyl or alkylthioalkyl, unsubstituted of substituted cycloalkyl or cycloalkenyl, an unsubstituted or substituted 5-membered saturated heterocyclic structure having one or two oxygen and/or sulfur atoms as hetero atoms
an unsubstituted or substituted 6-membered or 7-membered heterocyclic structure having not more than two oxygen and/or sulfur atoms and not more than two double bonds,
an unsubstituted or substituted 5-membered heteroaromatic structure having not more than two nitrogen atoms and/or one oxygen atom or one sulfur atom,
unsubstituted or substituted phenyl or pyridyl, and their agriculturally useful salts and esters of C$_1$-C$_{10}$-carboxylic acids and inorganic acids, processes and intermediates for their preparation and their use as herbicides.

5 Claims, No Drawings

CYCLOHEXENONE OXIME ETHERS, THEIR PREPARATION AND THEIR USE AS HERBICIDES

This application is a continuation of application Ser. No. 07/935,359, filed on Aug. 27, 1992 (now abandoned) which is a continuation of Ser. No. 07/697,057, filed on May 8, 1991 (now abandoned).

The present invention relates to novel herbicidal cyclohexenone oxime ethers of the formula I

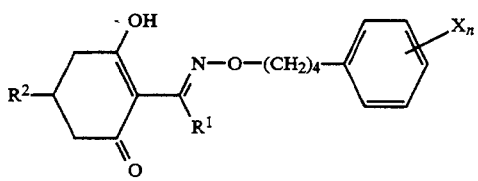

where
R$^1$ is C$_1$–C$_6$-alkyl,
X is halogen,
n is from 1 to 5,
R$^2$ is C$_1$–C$_4$-alkoxy-C$_1$–C$_6$-alkyl or C$_1$–C$_4$-alkylthio-C$_1$–C$_6$-alkyl,
C$_3$–C$_7$-cycloalkyl or C$_5$–C$_7$-cycloalkenyl, and these groups may additionally carry from one to three radicals selected from the group consisting of C$_1$–C$_4$-alkyl, C$_1$–C$_4$-alkoxy, C$_1$–C$_4$-alkylthio, C$_1$–C$_4$-haloalkyl, hydroxyl and halogen,
a 5-membered saturated heterocyclic structure which contains one or two hetero atoms selected from the group consisting of oxygen and sulfur and may additionally carry from one to three radicals selected from the group consisting C$_1$–C$_4$-alkyl, C$_1$–C$_4$-alkoxy, C$_1$–C$_4$-alkylthio and C$_1$–C$_4$-haloalkyl,
a 6-membered or 7-membered saturated or mono- or diunsaturated heterocyclic structure containing one or two hetero atoms selected from the group consisting of oxygen and sulfur, and the heterocyclic structure may additionally carry from one to three radicals selected from the group consisting of hydroxyl, halogen, C$_1$–C$_4$-alkyl, C$_1$–C$_4$-alkoxy, C$_1$–C$_4$-alkylthio and C$_1$–C$_4$-haloalkyl,
a 5-membered heteroaromatic structure containing one to three hetero atoms selected from the group consisting of two nitrogen atoms and one oxygen or sulfur atom, and this ring may additionally carry from one to three radicals selected from the group consisting of halogen, cyano, C$_1$–C$_4$-alkyl, C$_1$–C$_4$-alkoxy, C$_1$–C$_4$-alkylthio, C$_1$–C$_4$-haloalkyl, C$_2$–C$_6$-alkenyl, C$_2$–C$_6$-alkenyloxy, C$_2$–C$_6$-haloalkenyl and C$_1$–C$_4$-alkoxy- C$_1$–C$_4$-alkyl, phenyl or pyridyl, and these groups may additionally carry from one to three radicals selected from the group consisting of halogen, nitro, cyano, C$_1$–C$_4$-alkyl, C$_1$–C$_4$-alkoxy, C$_1$–C$_4$-alkylthio, C$_1$–C$_4$-haloalkyl, C$_3$–C$_6$-alkenyloxy, C$_3$–C$_6$-alkynyloxy and —NR$^3$R$^4$, where
R$^3$ is hydrogen, C$_1$–C$_4$-alkyl, C$_3$–C$_6$-alkenyl or C$_3$–C$_6$-alkynyl and
R$^4$ is hydrogen, C$_1$–C$_4$-alkyl, C$_3$–C$_6$-alkenyl, C$_3$–C$_6$-alkynyl, C$_1$–C$_6$-acyl or benzoyl, and the aromatic ring may additionally carry from one to three radicals selected from the group consisting of nitro, cyano, halogen, C$_1$–C$_4$-alkyl, C$_1$–C$_4$-alkoxy, C$_1$–C$_4$-alkylthio and C$_1$–C$_4$-haloalkyl, and their agriculturally usable salts and esters of C$_1$–C$_{10}$-carboxylic acids and inorganic acids.

The present invention furthermore relates to a process for their preparation and their use as crop protection agents.

The novel cyclohexenones I obviously have acidic character, i.e. they can form simple reaction products, such as salts of alkali metal or alkaline earth metal compounds or enol esters.

The compounds of the formula I may occur in a plurality of tautomeric forms, all of which are embraced by the claim.

DE-A 38 38 309 describes herbicidal cyclohexenone oxime ethers whose general formula covers the arylbutyleneoximinocyclohexanediones I defined at the outset. Compounds of the formula I'

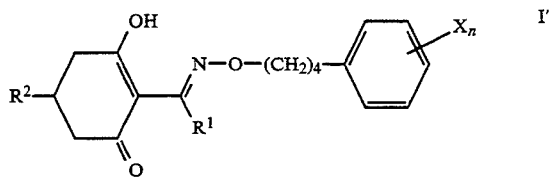

where X is p-trifluoromethyl or p-tert-butyl, n is 0 or 1 and R$^1$ and R$^2$ have the meanings stated under I, are mentioned in particular.

It is an object of the present invention to synthesize cyclohexenone oxime ethers which have high selectivity compared with the known members of this class of substances in controlling weeds in gramineous crops, such as rice.

We have found that this object is achieved by the novel cyclohexenone oxime ethers of the formula I which are defined at the outset and which have a good herbicidal action, preferably against species from the grass family (Gramineae). They are tolerated and hence selective in broad-leaved crops and in monocotyledon cultures which do not belong to the Gramineae. They also include compounds which exhibit selectivity also in gramineous crops and at the same time control undesirable grasses.

The cyclohexenones of the formula I can be prepared in a conventional manner from derivatives of the formula II (EP-A 80 301, EP-A-125 094, EP-A-142 741, U.S. Pat. No. 4,249,937, EP-A 137 174 and EP-A 177 913) and the corresponding hydroxylamines of the formula III (EP-A 169 521).

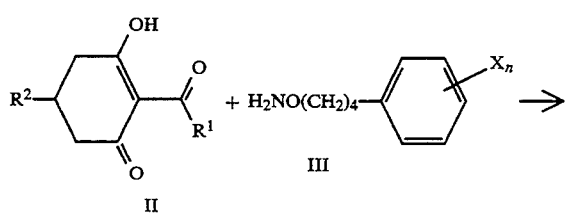

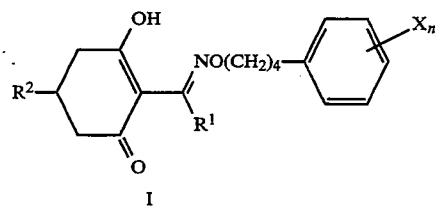

I

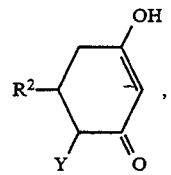

IV

The reaction is advantageously carried out in the heterogeneous phase in a solvent, at an adequate temperature below about 80° C., in the presence of a base, and the hydroxylamine III is used in the form of its ammonium salt.

Examples of suitable bases are carbonates, bicarbonates, acetates, alcoholates or oxides of alkali or alkaline earth metals, in particular sodiumhydroxide, potassium hydroxide, magnesium oxide and calcium oxide. Organic bases, such as pyridine or tertiary amines, can also be used. The base is added, for example, in an amount of from 0.5 to 2 mole equivalents, based on the ammonium compound.

Examples of suitable solvents are dimethyl sulfoxide, alcohols, such as methanol, ethanol and isopropanol, aromatic hydrocarbons, such as benzene and toluene, chlorohydrocarbons, such as chloroform and dichloroethane, aliphatic hydrocarbons, such as hexane and cyclohexane, esters, such as ethyl acetate, and ethers, such as diethyl ether, dioxane and tetrahydrofuran. The reaction is preferably carried out in methanol using sodium bicarbonate as the base.

The reaction is complete after a few hours. The desired compound can be isolated, for example by evaporating down the mixture, distributing the residue in methylene chloride/water and distilling off the solvent under reduced pressure.

However, the free hydroxylamine base, for example in the form of an aqueous solution, can also be used directly for this reaction; depending on the solvent used for the compound II, a single-phase or two-phase reaction mixture is obtained.

Examples of suitable solvents for this variant are alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

Alkali metal salts of the compounds I can be obtained by treating the 3-hydroxy compounds with sodium hydroxide, potassium hydroxide or a sodium or potassium alcoholate in aqueous solution or in an organic solvent, such as methanol, ethanol, acetone or toluene.

Other metal salts, such as manganese, copper, zinc, iron, calcium, magnesium and barium salts, can be prepared from the sodium salts in a conventional manner, as can ammonium and phosphonium salts using ammonia or phosphonium, sulfonium or sulfoxonium hydroxide.

The compounds of type II can be prepared, for example, from the corresponding cyclohexane-1,3-diones of the formula IV where Y is hydrogen or methoxycarbonyl, by known methods, for example as described in Tetrahedron Lett. (1975), 2491.

It is also possible to prepare the compounds of the formula II by the enol ester intermediates V which are obtained in the reaction of compounds of the formula IV with acyl chlorides VI in the presence of a base and are then subjected to a rearrangement reaction with certain imidazole or pyridine derivatives (Japanese Preliminary Published Application 79/063 052).

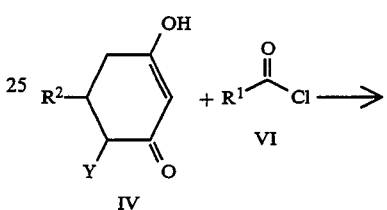

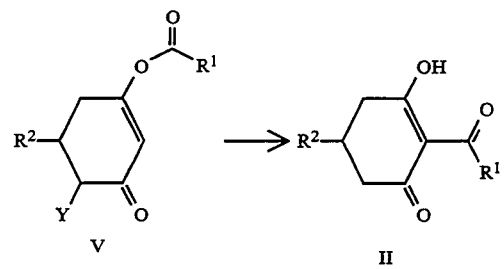

The compounds of the formula IV are obtained by a number of known process steps, starting from known intermediates.

The synthesis of the hydroxylamines III is carried out according to the reaction scheme below, for example by
A) alkylation of N-hydroxyphthalimide VII with suitable phenylbutyl halides VIII and subsequent elimination of the protective group, for example with hydrazine or ethanolamine, similarly to Examples in EP-A-244 786 or Houben-Weyl, Methoden der organischen Chemie, Volume X/1, page 1152 et seq. or
B) hydrogenation of N-4-phenylbutenyloxyphthalimides Xa, b, whose preparation is described in DE-A 38 38 310, by means of suitable catalysts, e.g. palladium on active carbon, in suitable inert solvents, such as methanol, tetrahydrofuran or dioxane, and subsequent elimination of the protective group as described above.

The hydrogenation is advantageously carried out at from 20° C. to the boiling point of the solvent, in particular at room temperature, by a conventional method, under atmospheric, superatmospheric or reduced pressure. A pressure range of from 1 to 10, in particular 1 to 2, bar is preferred.

Reaction scheme:

Route A)

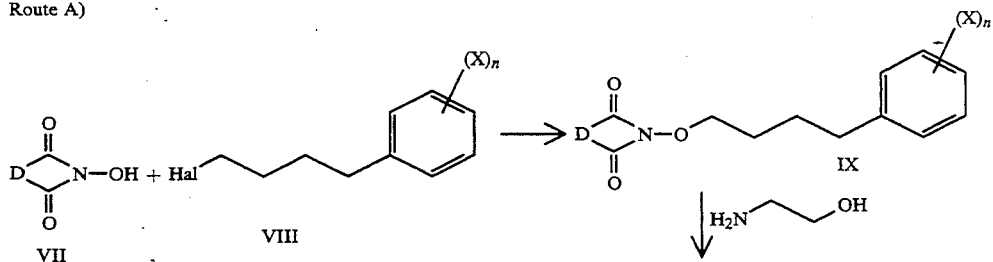

Route B)

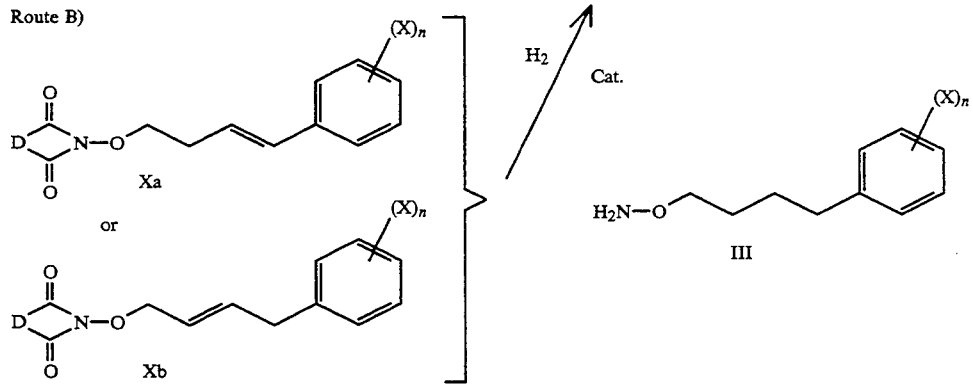

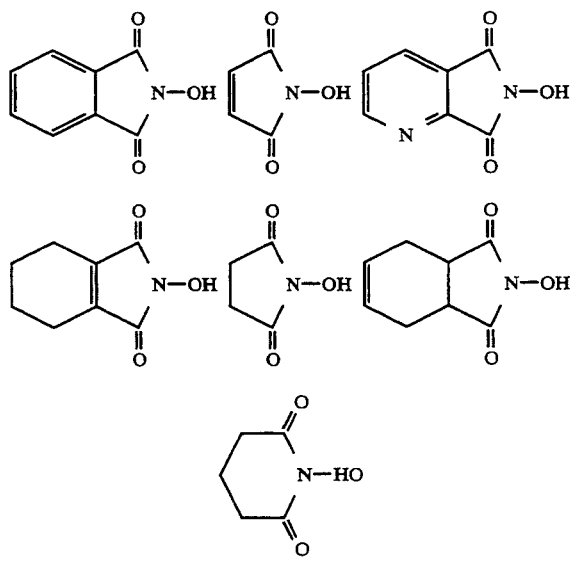

In the cyclic hydroximides VII, D is, for example, $C_2$–$C_3$-alkylene, $C_2$-alkenylene or a 5-membered or 6-membered ring which contains not more than 3 double bonds and may contain 1 nitrogen atom, for example phenylene, pyridinylene, cyclopentylene, cyclohexylene or cyclohexenylene. Examples of suitable substances are the following:

The cleavage of the cyclic imide ethers VIII is carried out similarly to a process described in EP-A 244 786, using alkanolamines. After this process, hydroxylamines III can be isolated as free bases or, after precipitation with acids, as salts. Readily crystallizing salts are obtained by reacting the bases with oxalic acid.

In view of the biological activity, preferred cyclohexenones of the formula I are those in which $R^1$ is alkyl, such as methyl, ethyl, propyl or n-butyl, in particular ethyl or propyl, X is halogen, such as fluorine, chlorine, bromine or iodine, in particular fluorine or chlorine, n is from 1 to 5, in particular 1, 2 or 3, the substituents being identical or different where there is a plurality of radicals X, $R^2$ is alkyl as stated under $R^1$, which may carry an alkoxy or alkylthio group stated below, preferably in the 1-, 2- or 3-position, in particular 2-ethylthiopropyl, or cyclohexyl which may carry from 1 to 3 methyl or hydroxyl groups, in particular 4-methylcyclohexyl or 3,4-dihydroxycyclohexyl, 5-membered hetaryl, such as pyrazolyl or isoxazolyl, a 6-membered heterocyclic structure, such as tetrahydropyran-3-yl, tetrahydropyran-4-yl or tetrahydrothiopyran3-yl, phenyl or pyridyl, where the cyclic radicals may carry from one to three alkyl, alkoxy, alkylthio and/or haloalkyl groups and, in the case of 6-membered radicals, also halogen as stated under X or hydroxyl, for example alkyl, such as methyl ethyl, propyl, 1-methylethyl, butyl, 1-methylpropyl, 2-methylpropyl or 1,1-dimethylethyl, in particular methyl or 1,1-dimethylethyl, alkoxy, such as methoxy, ethoxy, propoxy, 1-methylethoxy, butoxy, 1-methylpropoxy, 2-methylpropoxy or 1,1-dimethylethoxy, in particular methoxy, ethoxy, 1-methylethoxy or 1,1-dimethylethoxy, alkylthio, such as methylthio, ethylthio, propylthio, 1-methylethylthio, butylthio, 1-methylpropylthio, 2-methylpropylthio or 1,1-dimethylethylthio, in particular methylthio, or haloalkyl such as fluoromethyl, difluoromethyl, trifluoromethyl, chlorodifluoromethyl, dichlorofluoromethyl or trichloromethyl, in particular difluoromethyl or trifluoromethyl.

2,4,6-Trimethylphenyl is particularly preferred.

The 5-membered heteroaromatic radicals $R^2$ may carry the following radicals as substituents:

halogen as stated under X, in particular fluorine or chlorine.

In the case of the phenyl and pyridyl radicals, suitable substituents in addition to the abovementioned groups are the following radicals:

alkynyloxy, such as 2-propynyloxy, in particular propargyloxyphenyl or amino which may carry one or two acyl radicals, such as acetyl or benzoyl.

Particularly preferred cyclohexenone oxime ethers of the formula I are summarized in the Table below:

TABLE 1

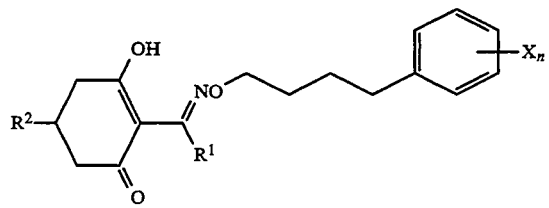

| No. | $R^1$ | $R^2$ | $X_n$ | phys. data [NMR*) ($\delta$ in ppm)] |
|---|---|---|---|---|
| 1.01 | Ethyl | Tetrahydropyran-3-yl | 4-Fluoro | 2.9(broad, 2H); 4.1(broad, 2H) |
| 1.02 | Propyl | Tetrahydropyran-3-yl | 4-Fluoro | 2.9(t, 2H); 4.05(broad, 2H) |
| 1.03 | Ethyl | Tetrahydrothiopyran-3-yl | 4-Fluoro | 2.9(t, 2H); 4.05(broad, 2H) |
| 1.04 | Propyl | Tetrahydrothiopyran-3-yl | 4-Fluoro | 2.9(t, 2H); 4.05(broad, 2H) |
| 1.05 | Ethyl | Tetrahydropyran-4-yl | 4-Fluoro | 4.05(broad, 2H) |
| 1.06 | Propyl | Tetrahydropyran-4-yl | 4-Fluoro | 4.05(broad, 2H) |
| 1.07 | Ethyl | Tetrahydropyran-3-yl | 4-Chloro | 2.9(t, 2H); 4.05(broad, 2H) |
| 1.08 | Propyl | Tetrahydropyran-3-yl | 4-Chloro | 2.9(t, 2H); 4.05(broad, 2H) |
| 1.09 | Ethyl | Tetrahydropyran-4-yl | 4-Chloro | 2.9(t, 2H); 4.05(broad, 2H) |
| 1.10 | Propyl | Tetrahydropyran-4-yl | 4-Chloro | 2.9(breit, 2H); 4.05(broad, 2H) |
| 1.11 | Ethyl | Tetrahydrothiopyran-3-yl | 4-Chloro | 4.05(broad, 2H) |
| 1.12 | Propyl | Tetrahydrothiopyran-3-yl | 4-Chloro | 4.05(broad, 2H) |
| 1.13 | Ethyl | Tetrahydrothiopyran-3-yl | 3-Fluoro | 1.1(t, 3H); 2.9(q, 2H); 4.05(m, 2H) |
| 1.14 | Propyl | Tetrahydrothiopyran-3-yl | 3-Fluoro | 0.95(t, 3H); 2.9(q, 2H); 4.05(m, 2H) |
| 1.15 | Ethyl | Tetrahydropyran-3-yl | 3-Fluoro | 1.15(t, 3H); 3.2(m, 1H); 3.35(m, 1H); 4.05(m, 2H) |
| 1.16 | Propyl | Tetrahydropyran-3-yl | 3-Fluoro | 0.95(t, 3H); 3.15(m, 1H); 3.35(m, 1H); 4.05(m, 2H) |
| 1.17 | Ethyl | Tetrahydropyran-4-yl | 3-Fluoro | 1.1(t, 3H); 2.9(q, 2H); 3.35(m, 2H) |
| 1.18 | Propyl | Tetrahydropyran-4-yl | 3-Fluoro | 0.95(t, 3H); 2.9(m, 2H); 3.35(m, 2H) |
| 1.19 | Ethyl | Tetrahydrothiopyran-3-yl | 3-Chloro | 1.1(t, 3H); 2.9(m, 2H); 4.05(m, 2H) |
| 1.20 | Propyl | Tetrahydrothiopyran-3-yl | 3-Chloro | 0.95(t, 3H); 2.9(m, 2H); 4,05(m, 2H) |
| 1.21 | Ethyl | Tetrahydropyran-3-yl | 3-Chloro | 1.1(t, 3H); 2.9(m, 2H); 3.18(m, 1H); 3.35(m, 1H); 4.05(m, 2H) |
| 1.22 | Propyl | Tetrahydropyran-3-yl | 3-Chloro | 0.95 (t, 3H); 2.9(m, 2H); 3.15(m, 1H); 3.35(m, 1H); 4.05(m, 2H) |
| 1.23 | Ethyl | Tetrahydropyran-4-yl | 3-Chloro | 1.15(t, 3H); 2.9(m, 2H); 3.35(m, 2H) |
| 1.24 | Propyl | Tetrahydropyran-4-yl | 3-Chloro | 0.95(t, 3H); 2.9(m, 2H); 3.38(m, 2H) |
| 1.25 | Propyl | 2-Ethylthiopropyl | 4-Chloro | 0.95(t, 3H); 1.25(t, 3H); 1.35(t, 3H); 4.05(m, 2H) |
| 1.26 | Ethyl | Tetrahydrothiopyran-3-yl | 2,6-Dichloro | 1.15(t, 3H); 4.05(t, 2H); 7.05(dd, 1H); 7.25(d, 2H) |
| 1.27 | Propyl | Tetrahydrothiopyran-3-yl | 2,6-Dichloro | 0.95(t, 3H); 4.05(t, 2H); 7.05(dd, 1H); 7.25(d, 2H) |
| 1.28 | Ethyl | Tetrahydropyran-4-yl | 2,6-Dichloro | 1.15(t, 3H); 3.35(m, 2H); 4.1(t, 2H); 7.05(dd, 1H) |
| 1.29 | Propyl | Tetrahydropyran-4-yl | 2,6-Dichloro | 0.95(t, 3H); 3.35(m, 2H); 4.1(t, 2H); 7.05(dd, 1H) |
| 1.30 | Propyl | Pyridin-3-yl | 2,6-DichlOro | 0.95(t, 3H); 4.1(t, 2H); 7.05(dd, 1H); 7.55(m, 1H) |
| 1.31 | Ethyl | Furan-2-yl | 2,6-Dichloro | 1.15(t, 3H); 4.1(t, 2H); 6.05(d, 1H); 7.05(dd, 1H) |
| 1.32 | Ethyl | 4-Benzoylaminophenyl | 2,6-Dichloro | 1.15(t, 3H); 4.1(t, 2H); 7.2(m, 5H); 7.85(m, 2H) |
| 1.33 | Propyl | 3,4-Dihydroxy-4-methylcyclohexyl | 2,6-Dichloro | 0.95(t, 3H); 1.25(s, 3H); 4.1(t, 2H); 7.05(dd, 1H) |
| 1.34 | Ethyl | Dioxolan-2-yl | 2,6-Dichloro | 1.15(t, 3H); 4.1(t, 2H); 4.8(d, 1H); 7.05(dd, 1H) |
| 1.35 | Propyl | 4-Difluoromethoxyphenyl | 2,6-Dichloro | 0.95(t, 3H); 4.1(t, 2H); 6.5(t, 1H); 7.1(m, 3H) |
| 1.36 | Ethyl | 4-Fluoro-3-nitrophenyl | 2,6-Dichloro | 1.15(t, 3H); 4.1(t, 2H); 7.05(dd, 1H); 7.95(dd, 1H) |
| 1.37 | Ethyl | Tetrahydrothiopyran-3-yl | 2,4-Dichloro | 1.15(t, 3H); 4.1(t, 2H); 7.15(m, 2H); 7.35(d, 1H) |
| 1.38 | Propyl | Tetrahydrothiopyran-3-yl | 2,4-Dichloro | 0.95(t, 3H); 4.1(t, 2H); 7.15(m, 2H); 7.35(d, 1H) |
| 1.39 | Ethyl | Tetrahydropyran-4-yl | 2,4-Dichloro | 1.15(t, 3H); 4.1(t, 2H); 7.15(m, 2H); 7.35(d, 1H) |
| 1.40 | Propyl | Tetrahydropyran-4-yl | 2,4-Dichloro | 0.95(t, 3H); 4.1(t, 2H); 7.15(m, 2H); |

TABLE 1-continued

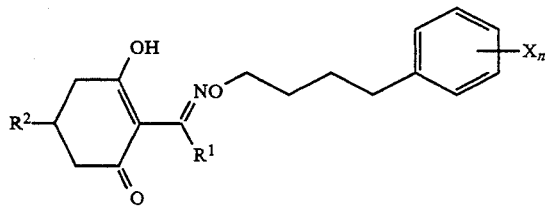

| No. | R¹ | R² | X_n | phys. data [NMR*] ($\delta$ in ppm)] |
|-----|----|----|-----|--------------------------------------|
|     | -  |    |     | 7.35(d, 1H)                          |

*selected data

The cyclohexenone oxime ethers I are suitable as herbicides, in particular for controlling plant species from among the Gramineae (grasses).

The cyclohexenone derivatives I or the herbicides containing them can be used, for example, in the form of directly sprayable solutions, powders, suspensions, including concentrated aqueous, oily or other suspensions or dispersions, emulsions, oil dispersions, pastes, dusting agents, broadcasting agents or granules, by spraying, atomizing, dusting, broadcasting or pouring. The application forms depend on the intended uses; they should in any case ensure very fine distribution of the novel active ingredients.

Compounds I are suitable in general for the preparation of directly sprayable solutions, emulsions, pastes or oil dispersions. Suitable inert additives are mineral oil fractions having a medium to high boiling point, such as kerosene or diesel oil, as well as coal tar oils and oils of vegetable or animal origin, aliphatic, cyclic and aromatic hydrocarbons, e.g. toluene, xylene, paraffin, tetrahydronaphthalene, alkylated naphthalenes and derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates, as such or in solution in oil or solvent, can be homogenized in water by means of wetting agents, adhesives, dispersants or emulsifiers. However, it is also possible for concentrates which consist of active substances, wetting agents, adhesives, dispersants or emulsifiers and may consist of solvents or oil and which are suitable for dilution with water to be prepared.

Suitable surfactants are the alkali metal, alkaline earth metal and ammonium salts of aromatic sulfonic acids, for example lignin-, phenol-, naphthalene- and dibutylnaphthalenesulfonic acid, and of fatty acids, alkyl- and alkylarylsulfonates, alkylsulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ethers, ethoxylated isocotyl-, octyl-or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, broadcasting agents and dusting agents can be prepared by mixing or milling the active substances together with a solid carrier.

Granules, for example, coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, milled plastics, fertilizers, such as ammonium sulfate, ammonium phosphate, ammonium nitrate, ureas and vegetable products, such as cereal meal, ground bark, woodmeal and nutshell meal, cellulose powder and other solid carriers.

The formulations contain from 0.02 to 95, preferably from 0.5 to 90%, by weight of active ingredient. The active ingredients are used in a purity of from 90 to 100% preferably from 95 to 100% (according to the NMR spectrum).

The novel compounds I can be formulated, for example, as follows:

I. 90 parts by weight of compound No. 1.05 are mixed with 10 parts by weight of N-methyl-α-pyrrolidone, and a solution suitable for use in the form of very small drops is obtained.

II. 20 parts by weight of compound No. 1.03 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of the calcium salt of dodecyl benzenesulfonic acid and 5 parts by weight of an adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

III. 20 parts by weight of compound No. 1.11 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

IV. 20 parts by weight of active ingredient No. 1.11 are dissolved in a mixture which consists of 25 parts by weight of cyclohexanone, 65 parts by weight of a mineral oil fraction boiling within a range from 210° to 280° C. and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

V. 20 parts by weight of active ingredient No. 1.05 are thoroughly mixed with 3 parts by weight of the sodium salt of diisobutylnaphthalene-α-sulfonic acid, 17 parts by weight of the sodium salt of ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 1.03 are mixed with 97 parts by weight of finely divided kaolin. A dusting agent which contains 3% by weight of the active ingredient is obtained in this manner.

VII. 30 parts by weight of active ingredient No. 1.05 are thoroughly mixed with a mixture of 92 parts by weight of silica gel powder and 8 parts by weight of liquid paraffin which has been sprayed onto the surface of this silica gel. A formulation of the active ingredient having good adhesion is obtained in this manner.

VIII. 20 parts by weight of active ingredient No. 1.03 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The agents can be applied by the preemergence or postemergence method. If the active ingredients are less well tolerated by certain crops, it is also possible to use application methods in which the herbicides are sprayed with the aid of the sprayers in such a way that there is as far as possible no contact with the leaves of the sensitive crops while the active ingredients reach the leaves of undesirable plants growing underneath or reach the uncovered soil area (post-directed, lay-by).

The application rates of active ingredient are from 0.001 to 3, preferably from 0.01 to 2.0, kg/ha, depending on the season, the target plants and the stage of growth.

In view of the practicable action spectrum for weed control, the toleration by crops or the desired effect on the growth thereof and because of the wide range of application methods, the novel compounds can be used in a large number of crops. Examples of suitable crops are the following:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Brassica napus var. napus | rapeseed |
| Brassica napus var. napobrassica | swedes |
| Brassica rapa var. silvestris | beets |

-continued

| Botanical name | Common name |
| --- | --- |
| Camellia sinensis | tea plants |
| Carthamus tinctorius | safflower |
| Carya illinoinensis | pecan trees |
| Citrus limon | lemon trees |
| Citrus sinensis | orange trees |
| Coffea arabica (Coffea canephora, Coffea liberica) | coffee plants |
| Cucumis sativus | cucumbers |
| Cynodon dactylon | Bermudagrass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus dulcis | almond trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

To broaden the action spectrum and to achieve synergistic effects, the cyclohexenone derivatives of the formula I can be mixed both with one another and with members of other groups of herbicidal or growth-regulating active ingredients and applied together. Examples of suitable components for the mixture are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, quinolinecarboxylic acids, sulfonylurea derivatives, cyclohexenones, (hetero)aryloxyphenoxypropionic acids, their salts, esters and amides and others.

It may also be useful to apply the cyclohexenone derivatives of the formula I, or herbicides containing them, alone or together in combination with other herbicides or mixed with further crop protection agents, for example with pesticides, agents for controlling phytopathogenic fungi or bactericides. The miscibility with mineral salt solutions which are used for eliminating nutrient and trace element deficiencies is also of interest. It is also possible to add nonphytotoxic oils and oil concentrates.

EXAMPLES

4-Phenylbutoxyamine

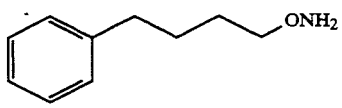

Method A 167.5 g (1.21 mol) of potassium carbonate and 2 g of potassium iodide were added to 302 g (1.85 mol) of N-hydroxyphthalimide in 1.9 l of anhydrous N-methylpyrrolidone. After the reaction mixture had been heated to 60° C., 395.2 g (1.85 mol) of 4-phenylbutyl bromide were added and this temperature was maintained for a further 6 hours. After cooling, the mixture was poured onto 6 l of ice water and taken up with dichloroethane, and the organic phase was washed with dilute sodium hydroxide solution, dried and evaporated down under reduced pressure. Yield: 379 g of N-(4-phenylbutoxy)-phthalimide (73%).

250-MHz $^1$H-NMR (DMSO-d$_6$) δ (ppm)=1.65-1.85 (m, 4H); 2.66 (t, 2H); 4.18 (t, 2H) 7.1-7.4 (m, 5H); 7.86 (s, 4H)

81.8 g (1.34 mol) of ethanolamine were added to 396 g (1.34 mol) of the phthalimidoether obtained above in 1,300 ml of ethyl acetate. The reaction mixture was heated at 60° C. for 5 hours. Thereafter, stirring was carried out for 24 hours at room temperature, the precipitated crystals were filtered off under suction and washed with a little ethyl acetate and a vigorous stream of hydrogen chloride gas was passed through the combined mother liquors for 15 minutes, during which the internal temperature should not exceed 40° C. The precipitated crystals were filtered off under suction, washed with a little ethyl acetate and dried under reduced pressure.

Yield:148.5 g of 4-phenylbutoxyamine hydrochloride (55%). Mp.:93°-94° C.

250-MHz $^1$H-NMR (DMSO-d$_6$) δ (ppm)=1.5-1.7 (m, 4H); 2.58 (t, 2H); 4.04 (t, 2H) 7.1-7.3 (m, 5H); 11.1 (broad s, 3H)

4-(4-Fluorophenyl)-butoxyamine

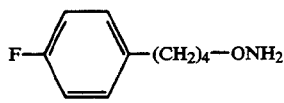

Method B: Hydrogenation
N-(4-(4-Fluorophenyl)-butoxy)-phthalimide 2 g of palladium on active carbon (10% strength) were added to a solution of 71.5 g (0.23 mol) of N-(4-(4-fluorophenyl)-3-butenyloxy)-phthalimide (prepared according to German Laid-Open Application DOS 3,838,310) in 300 ml of tetrahydrofuran. Hydrogenation was carried out under slightly superatmospheric pressure until 1.2 times the theoretical amount of hydrogen had been consumed. The mixture was filtered under suction over kieselguhr, the filtrate was evaporated down and the crude product was recrystallized from isopropanol.

Yield:62.8 g (87%); mp.:67°-68° C.

250-MHz $^1$H-NMR (DMSO-d$_6$) δ (ppm)=1.8-1.9 (m, 4H); 2.65 (t, 2H); 4.15 (t, 2H) 7.0-7.35 (m, 4H); 7.86 (s, 4H)

61.8 g (0.197 mol) of the phthalimidoether previously prepared were introduced a little at a time into 92 mol of ethanolamine. The mixture was heated at 60° C. for 3 hours, after which it was allowed to cool and was then poured into 400 ml of ice water and extracted with dichloroethane. The combined organic phases were washed with saturated sodiumchloride solution, dried and evaporated down under reduced pressure. The 4-(4-fluoro-phenyl)-butoxyamine was obtained as an oil.

250-MHz $^1$H-NMR (CDCl$_3$) δ (ppm)=1.5-1.74 (m, 4H); 2.61 (t, 2H); 3.68 (t, 2H) 5.4 (broad s, 2H); 6.9-7.2 (m, 4H)

4-(4-Chlorophenyl)-butoxyamine

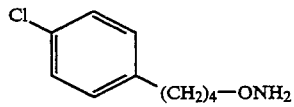

4-(4-Chlorophenyl)-butoxyamine was obtained as an oil in a total yield of 60% similarly to the Example described above, starting from N-(4-(4-chlorophenyl)-butenyloxyphthalimide (German Laid-Open Application DOS 3,838,310).

250-MHz $^1$H-NMR (CDCl$_3$) δ (ppm)=1.65-1.85 (m, 4H); 2.66 (t, 2H); 4.18 (t, 2H) 7.1-7.4 (m, 5H); 7.86 (s, 4H)

N-(4-(4-Chlorophenyl)-butoxyphthalimide

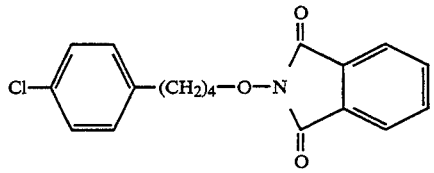

Mp.: 72°-73° C. (isopropanol) 250-MHz $^1$H-NMR (DMSO-d$_6$) δ (ppm)=1.6-1.85 (m, 4H); 2.68 (t, 2H); 4.17 (t, 2H) 7.2-7.4 (m, 4H); 7.88 (s, 4H)

2-{1-[4-(4-Fluorophenyl)-butoximino]-butyl}-5-tetrahydrothiopyran-3-yl-3-hydroxycyclohex-2-enone (compound 1.04)

2.2 g (12 mmol) of 4-(4-fluorophenyl)-butoxyamine were added to a solution of 3 g (11 mol) of 2-butyryl-3-hydroxy-5-tetrahydrothiopyran-3-ylcyclohex-2-enone in 100 ml of dry methanol. The mixture was stirred for 16 hours at room temperature and was then evaporated to dryness under reduced pressure. The residue was taken up in diethyl ether and the solution was chromatographed over silica gel. Yield:3.6 g (80% of theory).

The cyclohexenone compounds shown in Table I can be obtained similarly to this method.

Use Examples

The herbicidal action of the cyclohexenone oxime ethers of the formula I could be demonstrated by greenhouse experiments:

The culture vessels used were plastic flowerpots containing loamy sand with about 3% of humus as a substrate. The seeds of the test plants were sown separately according to species.

In the case of preemergence treatment, the active ingredients suspended or emulsified in water were applied directly after sowing, by means of nozzles providing a fine distribution. The vessels were lightly watered in order to promote germination and growth and then covered with transparent plastic covers until the plants had begun to grow. This covering ensures uniform germination of the test plants, unless this is adversely affected by the active ingredients.

For the purpose of postemergence treatment, the test plants were treated with the active ingredients suspended or emulsified in water, but only after reaching a height of growth of from 3 to 15 cm, depending on the growth form. The application rate for the postemergence treatment was 0.06 kg/ha of active substance.

The plants were kept at 10°–25° C. or 20°–35° C., depending on the species. The test period extended over 2-4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage or normal growth.

The plants used in the greenhouse experiments consisted of the following species:

| Latin name | Common name |
| --- | --- |
| Oryza sativa | rice |
| Echinochloa crus-galli | barnyardgrass |
| Setaria italica | foxtail millet |

When 0.06 kg/ha of active substance is used in the postemergence method, undesirable gramineous plants can be very readily controlled using Examples 1.11, 1.03 and 1.05, with simultaneous toleration by the example crop rice.

We claim:

1. A method for controlling undesirable plant growth in the presence of rice or wheat comprising treating the undesirable plants or the locus thereof with a herbicidally effective amount of a cyclohexenone oxime ether of the formula I

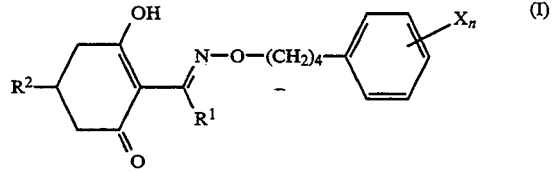

where
$R^1$ is $C_1$–$C_6$-alkyl,
X is halogen,
n is from 1 to 5,
$R^2$ is $C_1$–$C_4$-alkoxy-$C_1$–$C_6$-alkyl or $C_1$–$C_4$-alkylthio-$C_1$–$C_6$-alkyl,
$C_3$–$C_7$-cycloalkyl or $C_5$–$C_7$-cycloalkenyl, and these groups may additionally carry from one to three radicals selected from the group consisting of $C_1$–$C_4$-alkyl, $C_1$–$C_4$-alkoxy, $C_1$–$C_4$-alkylthio, $C_1$–$C_4$-haloalkyl, hydroxyl or halogen,
a 5-membered saturated heterocyclic structure which contains one or two hereto atoms chosen from oxygen or sulfur and may additionally carry from one to three radicals selected from the group consisting of $C_1$–$C_4$-alkyl, $C_1$–$C_4$-alkoxy, $C_1$–$C_4$-alkylthio or $C_1$–$C_4$-haloalkyl, a 6-membered or 7-membered saturated or mono- or diunsaturated heterocyclic structure containing one or two hereto atoms selected from the group consisting of oxygen or sulfur, and the heterocyclic structure may additionally carry from one to three radicals selected from the group consisting of hydroxyl, halogen, $C_1$–$C_4$-alkyl, $C_1$–$C_4$-alkoxy, $C_1$–$C_4$-alkylthio or $C_1$–$C_4$-haloalkyl,
a 5-membered heteroaromatic structure containing one to three hereto atoms selected from the group consisting of two nitrogen atoms or one oxygen or sulfur atom, and this ring may additionally carry from one to three radicals selected from the group consisting of halogen, cyano, $C_1$–$C_4$-alkyl, $C_1$–$C_4$-alkoxy, $C_1$–$C_4$-alkylthio, $C_1$–$C_4$-haloalkyl, $C_2$–$C_6$-alkenyl, $C_2$–$C_6$-alkenyloxy, $C_2$–$C_6$-haloalkenyl or $C_1$–$C_4$-alkoxy-$C_1$–$C_4$-alkyl, phenyl or pyridyl, and these groups may additionally carry from one to three radicals selected from the group consisting of halogen, nitro, cyano, $C_1$–$C_4$-alkyl, $C_1$–$C_4$-alkoxy, $C_1$–$C_4$-alkylthio, $C_1$–$C_4$-haloalkyl, $C_3$–$C_6$-alkenyloxy, $C_3$–$C_6$-alkynyloxy or —$NR^3R^4$,
where
$R^3$ is hydrogen, $C_1$–$C_4$-alkyl, $C_3$–$C_6$-alkenyl or $C_3$–$C_6$-alkynyl and
$R^4$ is hydrogen, $C_1$–$C_4$-alkyl, $C_3$–$C_6$-alkenyl, $C_3$–$C_6$-alkynyl, $C_1$–$C_6$-acyl or benzoyl, and the aromatic ring may additionally carry from one to three radicals selected from the group consisting of nitro, cyano, halogen, $C_1$–$C_4$-alkyl, $C_1$–$C_4$-alkoxy, $C_1$–$C_4$-alkylthio or $C_1$–$C_4$-haloalkyl, and its agriculturally usable salts and esters of $C_1$–$C_{10}$-carboxylic acids and inorganic acids in combination with an agriculturally acceptable carrier.

2. A method as set forth in claim 1, wherein $R^2$ is tetrahydrothiopyranyl.

3. A method as set forth in claim 2, wherein X is 4-chloro.

4. A method as set forth in claim 1, wherein $R^2$ is tetrahydropyranyl.

5. A method as set forth in claim 4, wherein X is 4-fluoro.

* * * * *

UNITED STATES PATENT AND TRADEMARK OFFICE
CERTIFICATE OF CORRECTION

PATENT NO. : 5,364,833
DATED : November 15, 1994
INVENTOR(S) : KAST et al.

It is certified that error appears in the above-indentified patent and that said Letters Patent is hereby corrected as shown below:

Claim 1, column 16, line 29:
"hereto" should read -- hetero --.

Claim 1, column 16, line 36:
"hereto" should read -- hetero --.

Signed and Sealed this

Thirty-first Day of January, 1995

*Attest:*

BRUCE LEHMAN

*Attesting Officer*  *Commissioner of Patents and Trademarks*